United States Patent [19]

Dähne et al.

[11] Patent Number: 4,655,225
[45] Date of Patent: Apr. 7, 1987

[54] SPECTROPHOTOMETRIC METHOD AND APPARATUS FOR THE NON-INVASIVE

[75] Inventors: Claus Dähne, Onex; Daniel Gross, Carouge, both of Switzerland

[73] Assignee: Kurabo Industries Ltd., Osaka, Japan

[21] Appl. No.: 724,667

[22] Filed: Apr. 18, 1985

[51] Int. Cl.[4] .............................................. A61B 6/00
[52] U.S. Cl. ..................................... 128/633; 128/664
[58] Field of Search ............................... 128/632-634, 128/664-667

[56] References Cited

U.S. PATENT DOCUMENTS

| | | | |
|---|---|---|---|
| 3,638,640 | 2/1972 | Shaw . | |
| 3,958,560 | 5/1976 | March . | |
| 4,223,680 | 9/1980 | Jobsis | 128/633 |
| 4,427,889 | 1/1984 | Muller | 128/633 X |

FOREIGN PATENT DOCUMENTS 2033575  5/1980  United Kingdom .
2075668 11/1981  United Kingdom .

OTHER PUBLICATIONS

Chemical Abstract Summary of "Hormone & Metabolic Res." (1979) Summaries CA 93, 200368 and 200369.

Primary Examiner—Kyle L. Howell
Assistant Examiner—John C. Hanley
Attorney, Agent, or Firm—Cushman, Darby & Cushman

[57] ABSTRACT

A directive light beam in a wavelength range appropriate for penetrating into body tissues is applied to a portion of a patient's body and the energy transmitted or back-scattered by the underlying tissue is analyzed spectrophotometrically for the presence of glucose. Analysis is performed using especially selected bands in the near-infrared region.

9 Claims, 10 Drawing Figures

SPECTROPHOTOMETRIC METHOD AND APPARATUS FOR THE NON-INVASIVE

FIELD OF INVENTION

The present invention concerns the photometric determination of glucose in the bloodstream or tissues of patients suspected to have developed diabetes. This determination is carried out by measuring the optical near infrared absorption of glucose in regions of the spectrum where typical glucose absorption bands exist and computing the measured values with reference values obtained from regions of the spectrum where glucose has no or little absorption and where the errors due to background absorptions by the constituents of the surrounding tissues or blood containing the glucose are of reduced significance or can be quantitatively compensated.

BACKGROUND OF THE ART

Many methods and devices have been developed up to now for the determination of glucose in vitro or in vivo by optical means.

For instance, in PCT application WO No. 81/00622, there is disclosed an IR absorption method and apparatus for determining glucose in body fluids. According to this reference, absorption spectra of serum or urine, both transmissive or reflective, i.e. due to back-scattering effects, are measured at two distinct wavelengths $\lambda 1$ and $\lambda 2$, $\lambda 2$ being typical of the absorption of a substance to be measured (for instance glucose) and $\lambda 1$ being a wavelength at which the absorption is roughly independent of the concentration of the substance of interest. Then the pertinent measured data are derived from calculating the ratio of the absorption values at $\lambda 1$ and $\lambda 2$, the bands of interest being in the range of 940–950 $cm^{-1}$ (10.64–10.54 $\mu m$) and 1090–1095 $cm^{-1}$ (9.17–9.13 $\mu m$), respectively. In this reference, the source of irradiation is provided by a $CO_2$ laser.

Swiss Pat. No. CH-612.271 discloses a non invasive method to determine biological substances in samples or through the skin using an attenuated total reflection (ATR) prism. This method relies on the passing of an infrared beam through a wave-guide (ATR prism) directly placed against a sample to be analyzed (for instance the lips or the tongue). The refractive index of the wave-guide being larger than that of the medium of the sample (optically thinner medium), the beam propagates therein following a totally reflected path, the only interaction thereof with said thinner medium (to be analyzed) being that of the "evanescent wave" component at the reflection site (see also Hormone & Metabolic Res./suppl. Ser. (1979), p. 30–35). When using predetermined infrared wavelengths typical of glucose absorption, the beam in the ATR prism is attenuated according to the glucose concentration in the optically thinner medium, this attenuation being ascertained and processed into glucose determination data. U.S. Pat. No. 3,958,560 discloses a non-invasive device for determining glucose in patient's eyes. Such device comprises a contact-lens shaped sensor device including an infrared source applied on one side of the cornea and a detector on the other side thereof. Thus, when a infrared radiation is applied to the area under measurement, light is transmitted through the cornea and the aqueous humor to the detector. The detected signal is transmitted to a remote receiver and a read-out device providing data on the concentration of glucose in the patient's eye as a function of the specific modifications undergone by the IR radiations when passing through the eye.

GB patent application No. 2,033,575 discloses a detector device for investigating substances in a patient's regions near to the bloodstream, namely $CO_2$, oxygen or glucose. The key features of such detector comprise radiation directing means arranged to direct optical radiation into the patient's body, and receiver means for detecting attenuated optical radiations backscattered or reflected within the patient's body i.e. from a region below the skin surface. The detected signal is thereafter processed into useful analytical data. Optical radiations include UV as well as IR radiations.

Other references rather refer to the measurement or monitoring of other bioactive parameters and components such as blood flow, metabolic oxyhemoglobin and desoxyhemoglobin but, in reason of their close analogies with the aforementioned techniques, they are also worth reviewing here. Thus U.S. Pat. No. 3,638,640 discloses a method and an apparatus for measuring oxygen and other substances in blood and living tissues. The apparatus comprises radiation sources and detectors disposed on a patient's body, for instance about the ear to measure the intensity passing therethrough or on the forehead to measure the radiation reflected therefrom after passing through the blood and skin tissue. The radiations used belong to the red and very near infrared region, for instance wavelengths ($\lambda$) of 660, 715 and 805 nm. The number of different wavelengths used simultaneously in the method is equal to the total of at least one measuring wavelength typical for each substance present in the area under investigation (including the substance(s) to be determined) plus one. By an appropriate electronic computation of the signals obtained after detection from absorption at these diverse wavelengths useful quantitative data on the concentrations of the substance to be measured are obtained irrespective of possible changes in measurement conditions such as displacement of the test appliance, changes in illumination intensity and geometry, changes in the amount of blood perfusing the tissue under investigation and the like.

GB patent application No. 2,075,668 describes a spectrophotometric apparatus for measuring and monitoring in-vivo and non-invasively the metabolism of body organs, e.g. changes in the oxido-reduction state of hemoglobin and cellular cytochrome as well as blood flow rates in various organs such as brain, heart, kidney and the like. The above objects are accomplished by optical techniques involving wavelengths in the 700–1300 nm range which have been shown to effectively penetrate the body tissues down to distances of several mm. Thus in FIG. 14 of this reference there is disclosed a device involving reflectance type measurements and comprising a light source for injecting light energy into a waveguide (optical fiber bundle) applied to the body and disposed in such way (slantwise relative to the skin) that the directionally emitted energy whch penetrates into the body through the skin is reflected or back scattered by the underlying tissue to be analyzed at some distance from the source; the partially absorbed energy then reaches a first detector placed also over the skin and somewhat distantly from the source. Another detector placed coaxially with the source picks up a back radiated reference signal, both the analytical and reference signals from the detectors being fed to a computing circuit, the output of which provides useful readout data concerning the sought after analytical information.

Although the aforementioned techniques have a lot of merit some difficulties inherent thereto still exist. These difficulties are mainly related to the optical properties of the radiations used for making the measurements. Thus, radiation penetration into the skin depends on the action of absorbing chromophores and is wavelength-dependent, i.e. the light in the infrared range above 2.5 μm is strongly absorbed by water and has very little penetration capability into living tissues containing glucose and, despite the highly specific absorption of the latter in this band, it is not readily usable to analyze body tissue volumes at depths exceeding a few microns or tens of microns. If exceptionally powerful sources (i.e. $CO_2$ laser) are used, deeper penetration is obtained but at the risk of burning the tissues under examination. Conversely, using wavelengths below about 1 micron (1000 nm) has the drawback that, although penetration in this region is fairly good, strong absorbing chromophores still exist such as hemoglobin, bilirubin ad melanin and specific absorptions due to glucose are extremely weak which provides insufficient or borderline sensitivity and accuracy for practical use in the medical field. In addition, the ATR method which tries to circumvent the adverse consequences of the heat effect by using the total internal reflection technique enables to investigate depths of tissues not exceeding about 10 μm which is insufficient to obtain reliable glucose determination information.

DISCLOSURE OF THE INVENTION

The present invention remedies these shortcomings. Indeed it was found quite unexpectedly that by operating at some wavelengths located in the 1000 to 2500 nm range, acceptable combinations of sufficient penetration depth to reach the tissues of interest and sufficient sensitivity in ascertaining glucose concentration variations could be accomplished, this being without risks of overheating tissues. At such penetration depths of, say, 0.5 mm to several mm, representative information on the conditions of patients could be gained in regard to possible lack or excess of glucose in the blood stream (hypo- or hyperglycemia). Therefore, one object of the invention is a spectrophotometric method for the transcutaneous non-invasive determination of glucose in patients suffering or suspected to suffer from diabetes in which a portion of said patient's body is irradiated with the light of a directional optical lamp source, the resulting energy I either transmitted or diffusely reflected (backscattered) by a sample volume of body tissue underneath the skin of said body portion being collected and converted into suitable electrical signals, said collected light including at least one spectral band of a first kind containing a measuring signal wavelength $\lambda G$ typical of the glucose absorption and at least another band of a second kind with a reference signal wavelength $\lambda R$ typical of the background absorption spectrum due to the tissue containing the glucose but in which the absorption of the latter is nil or insignificant, and in which method said electrical signals (the value of which, IG and IR, are representative of the absorption in said measuring and reference bands, respectively) are fed to an electronic computing circuit for being transformed into glucose concentration readouts, characterized in that the bands of the first and second kind below to the 1000 to 2500 nm medium near-IR range, $\lambda G$ being selected from 1575, 1765, 2100 and 2270+ or −15 nm and $\lambda R$ being selected either in the range 1100 to 1300 nm or in narrow regions situated on both sides of the measuring bands but outside the area where glucose absorbs strongly.

Figure 1:
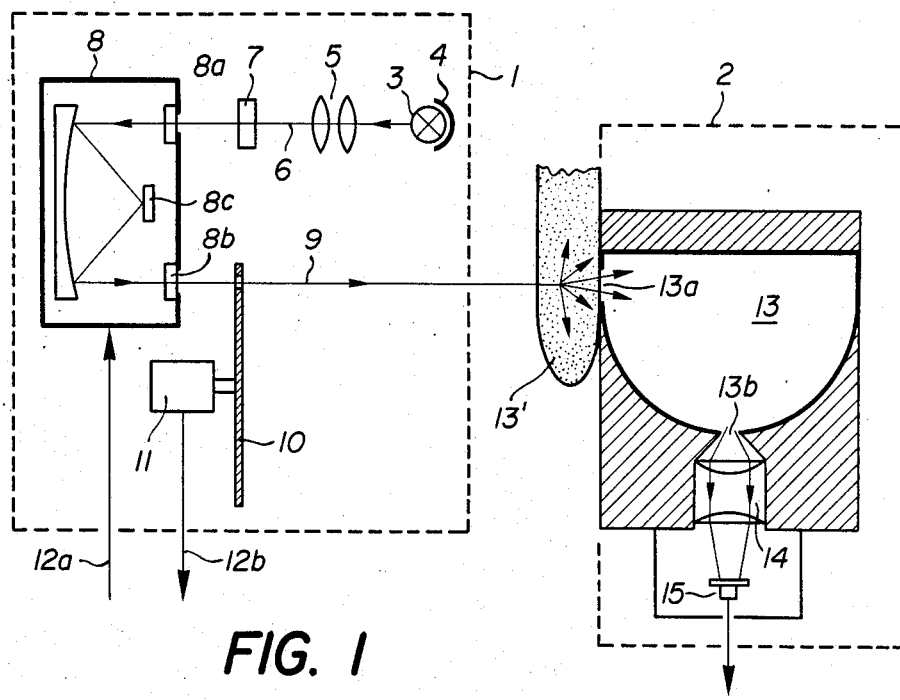
FIG. 1 represents schematically the main components of an apparatus for non-invasively measuring glucose in vivo by an absorptive transmission technique.

The light absorbed by the tissue subjected to analysis constitutes together with other losses due to scattered stray radiations inherent to the practice of the method and the apparatus components, the background response noise from which the useful signals must be separated. The absorbing entities in the body media containing the glucose include peptidic substances such as albumin, keratin, collagen and the like as well as low molecular weight species such as water, hydrogenocarbonate, salt and the like. These substances all have characteristic absorptions distinct from the aforementioned selected typical glucose absorptions as shown by the infrared spectra of FIGS. 5 to 10; and compensation can thus be afforded by subjecting the collected measuring and reference data to computation according to programmed algorithms. Further, the time concentration variation of the components depicted in FIGS. 5 to 10 in the blood and/or living tissues follows a pattern different from that of glucose in the measurement location, which difference is also usable to determine glucose in the presence of such components. Examples of possible computation algorithms are provided in the following reference: R. D. ROSENTHAL, an Introduction to Near Infrared Quantitative Analysis, 1977, Annual Meeting of American Association of Cereal Chemists.

According to one general method of computing applicable in the present invention a normalizing factor is first established from the differences in absorptions in the reference band when glucose is present or absent or in insignificant quantities in the tissue to be analyzed. Then this factor is used to normalize the measured value of glucose absorption in the $\lambda G$ band, the reference value being subtracted from the normalized value to provide the data for expressing the correct glucose concentration in the sample. The normalizing factor can be determined for instance by setting the reference's wavelength at an isosbestic point (i.e. a wavelength at which there is no significant change in absorption although the concentration of glucose may change).

Another way to obtain a normalizing factor is to focus alternately from the place where glucose should be analyzed to a place where the amount of glucose is either insignificant or constant and fairly well known, the background absorption spectrum being substantially constant or comparably shaped in the two locations. One will see hereinafter how this can be practically implemented.

According to another way of computing the absorption measured values into useful glucose determination results is to differentiate the IG and IR signals with regard to λ within the area of the bands of the first and of the second kind, respectively; and then to subtract one differential from the other and obtain the desired result from the difference. Reference to this method is provided in T. C. O'HAVER Potential Clinical Applications of Derivative and Wavelength Modulation Spectrometry, Clin. Chem. 25(a), 1548-53 (1959).

The invention also concerns an apparatus for carrying out the present analytical method.

This apparatus comprises a light source for directively applying a beam of light on a portion of a patient's body, the spectral composition of said light being such that it can penetrate through the skin to a region where glucose concentration can be measured with significance regarding the patient's conditions and from which said light can be gathered after being partially absorbed as a function of the glucose concentration, a collecting means for gathering the radiation transmitted or reflected (transflected) from said region, detector means for detecting and converting into electrical signals the gathered light as distinct wavelengths belonging to at least two bands, one measuring band and one reference band, and computing means to transform said electrical signals from useful readouts representative of the desired glucose measurement data. One characteristic feature of an embodiment of this apparatus is that it comprises means for varying continuously or stepwise the incidence angle relative to the body of said beam of light, said variation resulting in a consequent variation of the depth of the center of said region wherefrom the light is gathered after absorption.

Such an apparatus and variants thereof will now be described with the help of the annexed drawing.

The apparatus represented in FIG. 1 consists of two main sections, a light source section 1 and a detector section 2. The light source section 1 comprises a light source 3, for instance a halogen lamp and light directing means, for instance a reflector 4 and a condensor 5 for providing a directed beam 6 of light. This beam needs not be polarized or coherent but, of course, such types of light can also be used if desired. When using a wide band continuous spectrum of light, the apparatus also comprises a filter or system of filters 7 to block out undesired wavelength ranges mainly caused by higher order diffraction at the monochromator grating; in this particular application where the signals should be in the range of about 1000 to 2700 nm, visible ranges are eliminated by using a SCHOTT RG780 filter (0.8–1.3 μm), a silicon filter (1.3–2.2 μm) and a Ge filter (2.2–4.2 μm). The lamp is a 12 V, 100 W halogen lamp with the following properties: color temperature 3300° K.; maximum output at 850 nm; average luminance 3500 cd/cm$^2$. Of course, if monochromatic light sources were used in the present apparatus, for instance by means of tunable lasers, the blocking filters 7 would no longer be necessary.

The apparatus further comprises a monochromator 8 with inlet slit 8a and output slit 8b and a grating 8c. The monochromator can be of any suitable origin, for instance a JARREL-ASH model 70000 with sine bar wavelength drive is suitable. The monochromator can scan or repetitively shift from one selected wavelength to another one or, in succession, to several ones depending on whether one or more measuring and references wavelengths are used concurrently in the analysis. The shifting or scanning rate of the monochromator is programmed and controlled by the computer circuits to be described later and the signals thereto are provided by line 12a. Of course, if the source light is provided by means of lasers of specific wavelengths, the monochromator is no longer necessary.

The selected monochromatic beam 9 which emerges from the monochromator passes through a chopper disk 10 driven by a motor 11 whose rotation is controlled by a clock (not represented but conventionally inherent to any chopper system); this system also provides timing signals, the output of which is schematically represented by the arrow 12b, to be used for synchronizing the analog and digital electronic processing circuits as will be seen hereinafter. The periodical interruption of the excitation beam of light 9 by the chopper disk is required for removing or minimizing the background noise due to ambient light, detector dark noise, and other stray signals, i.e. the detector will alternately signal the background alone or the total of signal plus background from which the latter can be evaluated and compensated by sutracting the difference. As an example the chopper can operate with a 30 slot at a frequency of 500 Hz.

The detector section 2 of the apparatus is shown applied against an organ of the body to be investigated, for instance the ear lobe 13 in a manner such that the composite monochromatic beam 9 passes through that organ before reaching the detector section whereby it is attenuated by partial absorption and partial diffusion in the tissues under examination. As we have seen before, the main components of the body tissues competing with glucose as light absorbers in the spectral region of interest are the water and the proteins of the cells and interstitial fluid; however, the general distribution of these "background" constituents is fairly constant and so the general "shape" of the corresponding spectrum superimposed to that of glucose is also rather constant including the bands with points the intensity of which is substantially independent of the glucose concentration (isosbestic points). Therefore, as already mentioned, correlating the absorption of the background at the isosbestic points (wavelengths of reference) with the effective thickness of the tissue layer of the organ under investigation traversed by the incident beam enables to determine the reference absorption factor used for normalizing the absorption data made at the typical glucose λG wavelengths disclosed heretofore wherefrom the ultimate glucose concentration results are obtained.

In this connection, it should be noted that the principle of the aforementioned analysis can be expanded to analyze a three component mixture containing glucose, serum and water. Indeed, serum contains essentially all the dissolved constituents in blood or body fluid and, as mentioned above, several features in the absorption spectrum of serum are quite different from that of glucose. These features depicted from the curves of FIGS.

5 and 6 are emphasized in Table 1 below. Therefore the concentration of glucose can be estimated from absorbance measurements using at least three different wavelength.

TABLE 1

| Wavelength (nm) | Spectrum of serum | Spectrum of glucose |
| --- | --- | --- |
| 1 574 | flat | peak |
| 1 732 | peak | slope |
| 1 765 | dip | peak |
| 2 052 | peak | slope |
| 2 098 | dip | peak |
| 2 168 | peak | slope |
| 2 269 | slope | peak |
| 2 291 | peak | dip |
| 2 292 | — | peak |

Figure 5:
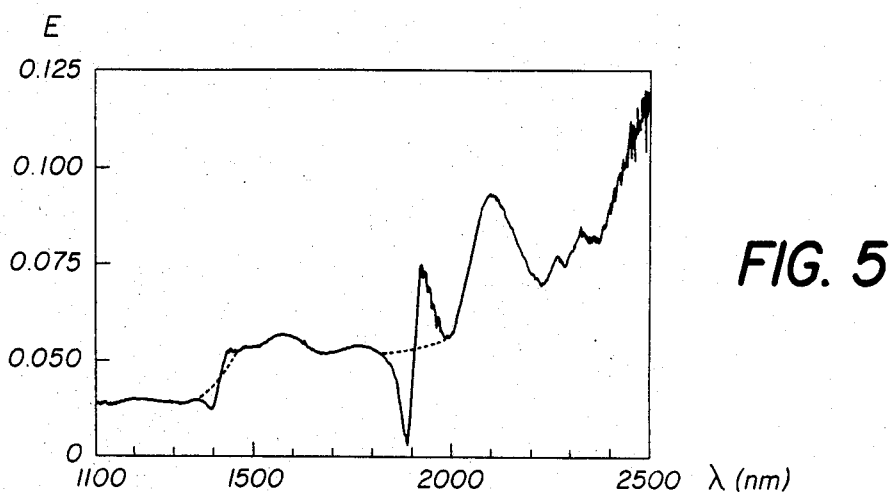
FIG. 5 represents an infrared spectrum of glucose (1 mole/1 aqueous solution) from which the corresponding infrared spectrum of water has been subtracted.
Figure 6:
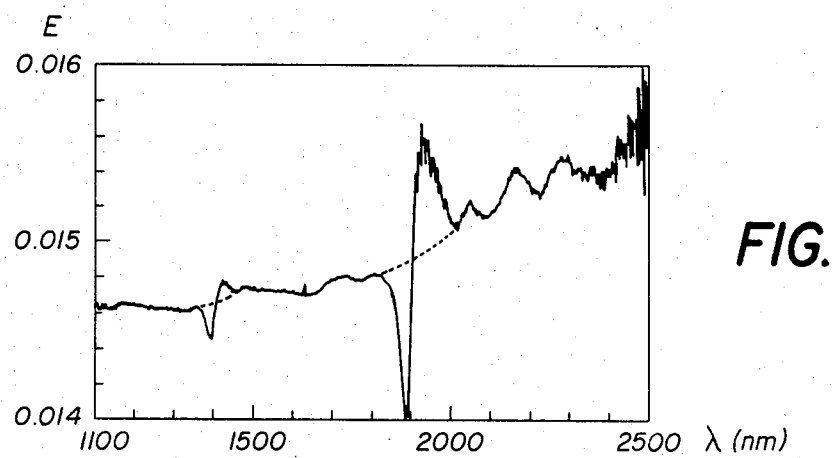
FIG. 6 is like FIG. 5 but refers to blood serum and water.
Figure 7:
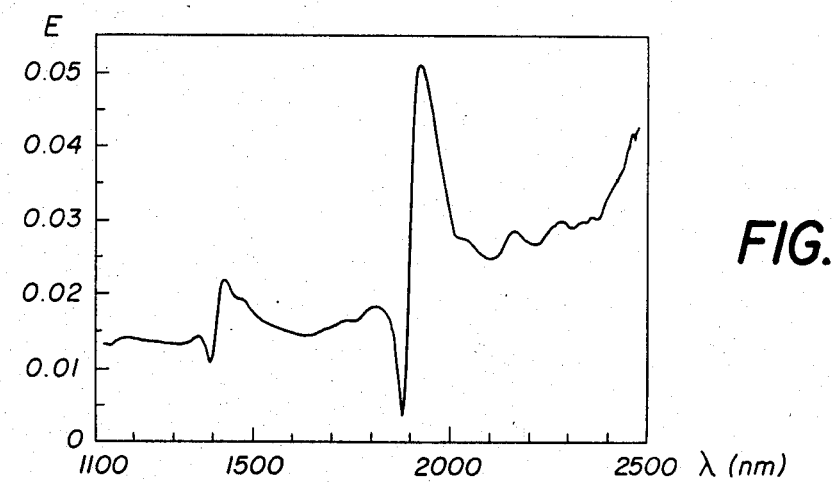
FIG. 7 is like FIG. 5 but refers to human serum albumin.
Figure 8:
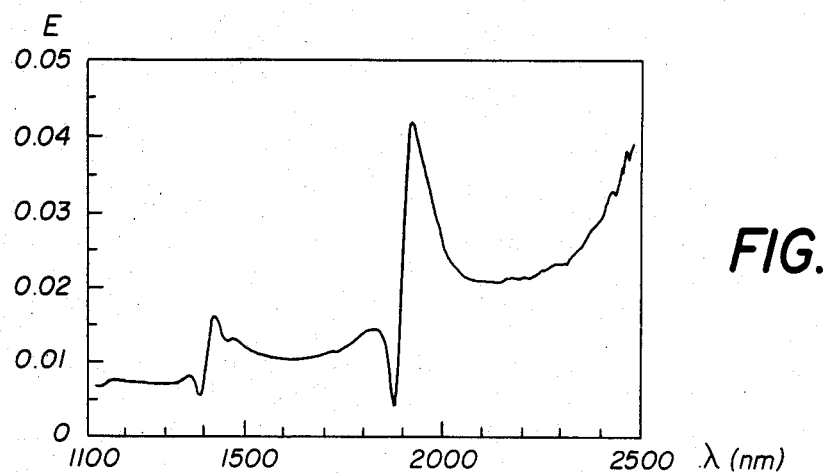
FIG. 8 is like FIG. 5 but refers to keratin.
Figure 9:
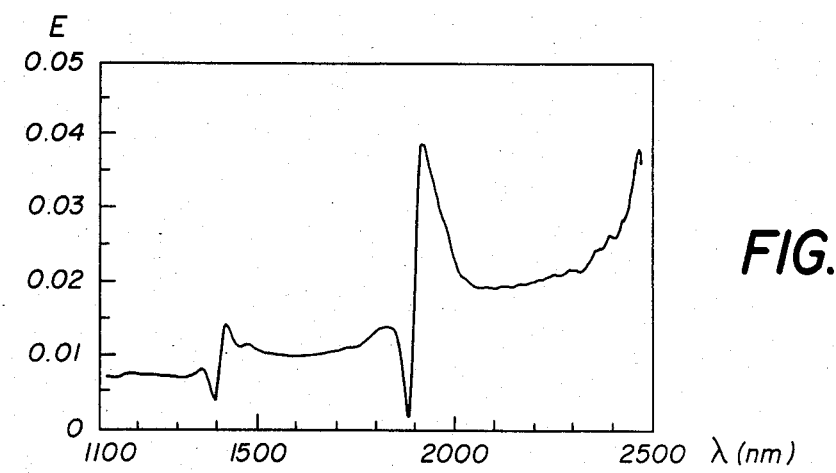
FIG. 9 is like FIG. 5 but refers to collagen.
Figure 10:
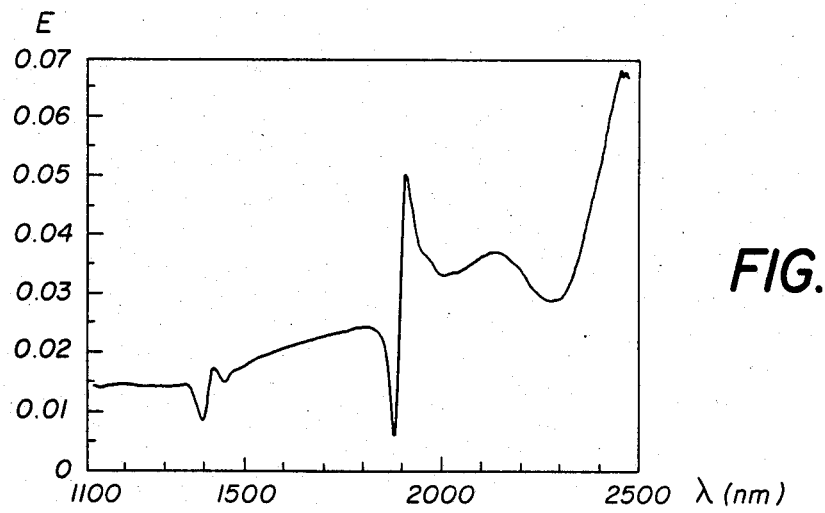
FIG. 10 is like FIG. 5 but refers to $HCO_3^-$.

By comparing FIG. 5 and FIG. 6, it is seen that very similar features still exist in the two spectra. These features are the followings:

1 100 to 1 350 nm, flat portion and 2 223 nm, dip portion.

The detector section 2 comprises a light collecting integrating sphere or half-sphere (sometimes referred to as Ulbricht sphere) the wall of which is layered with a dull high reflective coating for gathering and collecting all available light penetrating through an opening 13a of the device which is directly applied against the organ under investigation (the ear-lobe in this embodiment). Materials which are highly reflective in the 1 to 2.7 μm range are for instance Eastman 6080 white reflectance coating containing barium sulfate or gold plating, the latter having a better reflectance at the long wavelengths of the range. Using an integrating full sphere is generally preferred unless a half-sphere is necessary because of geometry considerations (see, for instance, the modification of FIG. 2). When this is required because of the positioning of the device about the ear, the integrating sphere is halved and its flat portion consists of a highly reflective mirror (gold coating). The performance of the half-sphere of this construction is somewhat less than that of the full sphere but still acceptable because the mirror optically mimics a full sphere. Differently stated, a full sphere is somewhat more efficient for collecting light but more bulky, so a compromise between sufficiently reduced physical size and sufficient efficiency is actually made in this embodiment. In the present drawing the curved portion of the half-sphere is presented as having ends somewhat flattened; however this should not be considered physically significant; the reason thereto being only of drafting convenience. The light collected by multiple reflection in the half-sphere escapes through opening 13b and is condensed by means of a condensor 14 to fall on a detector 15. Any detector sensitive to the range of wavelengths used here can be used; an example of such detector is a low temperature operating indium arsenide photodiode (JUDSON INFRARED INC. Pa 18936 USA) having the following properties.

| Model | J 12-D |
| --- | --- |
| Peak Wavelength | 2.8 μm |
| Operating Temperature | 77° K. |
| Time constant | 0.5-2 μsec |
| Size | 2 mm (diameter) |
| Responsivity | 1 A/W |
| D | $4.10^{11}$ cmHz$^{\frac{1}{2}}$W$^{-1}$ |
| Package | Metal Dewar |
| Liquid N$_2$ Hold Time | 6-8 hr |
| Field of view | 60° |

Light collector means different from the integrating sphere can also be used in the present invention. Such means consist of an arrangement of curved surface mirrors internal reflective ellipsoid or paraboloid surface portions) which collect the light exiting from the body tissues and focus it onto the detecting means. Such light collecting means may have improved collecting efficiency over that of the integrating sphere because of reduced number of reflections. Examples of collecting arrangements suitable for application in the invention can be found in the following references: N. W. WALLACE, the Optical Layout of off-axis paraboles: Photonics Spectra, September 1984, p. 55; HARRICK SCIENTIFIC CORP., Catalog HSC-83 (IR-Vis-UV accessories), Ossining, N.Y. 10562, USA.

The operation of the present apparatus is obvious from the previous description; for measuring the glucose in the ear tissue of a sitting patient, the detector 2 is affixed onto the inside portion of the ear lobe, for instance maintained by appropriate straps, and the monochromatic light from the source section 1 (usually mounted on an appropriate stand or rig on the side of the patient's chair) is directed on the external side of the ear portion directly facing the detector. The light beam 9 strikes the ear portion and after traversing it penetrates into the collecting half-sphere 13 wherefrom it goes to detector 15 whereby it is converted into an electrical signal. The beam 9 is interrupted regularly by the action of the chopper for the reasons explained before and, when in its non interrupted position, it provides an alternating dual or multiple wavelength incident light input generated in the monochromator said incident light comprising at least one measuring signal generally centered about the aforementioned values of 1575, 1765, 2100 or 2700 nm and at least one reference signal in the wide reference range or at the narrow wavelength ranges on both sides of the λG wavelengths. Thus the electrical signal obtained from detector 15 is a multiplex signal repetitively carrying the information relative to the optical apparatus background, the spectral background of the volume of matter being analyzed and the glucose absorption measurements according to a schedule under control of the chopper system 11 (line 12b) and the computer circuits (line 12a). We shall see hereinafter how this multiplex signal is decoded and processed.

Figure 2:
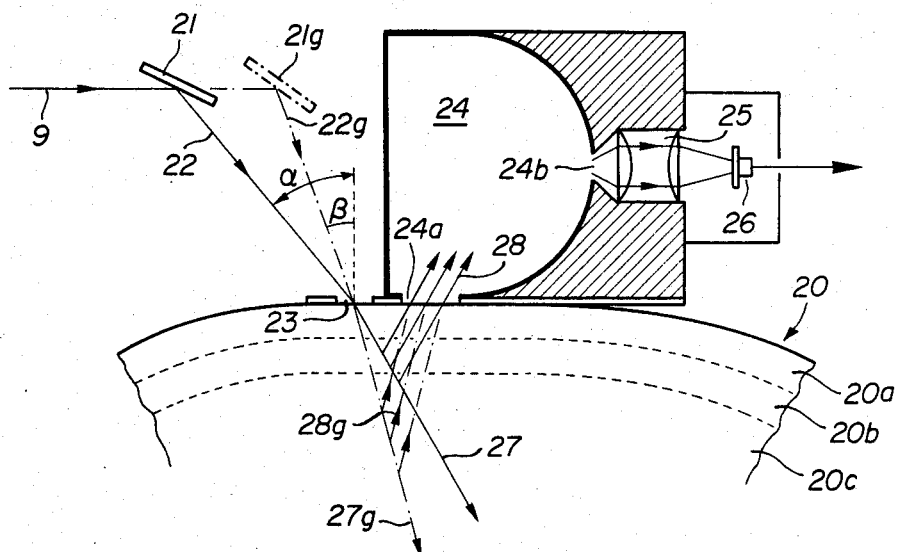
FIG. 2 represents schematically a detail of a variant of the apparatus of FIG. 1 designed to operate by an absorptive reflective technique.

Before doing so we shall turn to the modification of FIG. 2. This modification of which only a portion is represented in the drawing constitutes an integrated light source-detector device to be placed directly over the skin, i.e. a device that operates according to the principle of reflection or back-scattering of light by tissues under the skin. The reference and measuring light signal generator of this device is similar to that used in the case of the device of FIG. 1 up to the chopper disk; therefore the light emerging from said chopper is given the same numeral 9 in FIG. 2.

The integrated light source-detector device of FIG. 2 is represented as being applied on the skin 20 of a patient; said skin being arbitrarily represented by successive layers 20a, 20b and some underneath tissue 20c. The present device comprises a movable mirror 21 which can be displaced horizontally continuously or stepwise while maintained in reflecting relationship with beam 9 so that the reflected beam 22 is permanently directed into a horizontal slit 23 of the device. In order to more clearly illustrate this point, a ghost image 21g of the mirror 21 after being moved in a second position is provided on the drawing. The light beam 22 reflected by mirror 21 meets the skin at an incidence angle indicated by λ. When the mirror is displaced in position 21g, its orientation is such that the reflected beam 22g meets the skin at an angle β smaller than λ. The mechanical means to move and synchronously tilt the mirror 21 are conventional and not represented here. The present device further comprises as in the previous embodiment a collecting half-sphere 24 with an input opening 24a, a condensor 25 and a light detector 26 for converting the light gathered into an electric signal represented by an arrow in the drawing.

The operation of the present device, which is fairly obvious from its description, enables to undertake modulated depth glucose analysis below the skin. Indeed, during analysis, the mirror 21 can be moved back and forth so that the angle of penetration (α, β) of the beam 22 can be changed at will. The angles of the corresponding penetrating beams 27 and 27g will change accordingly and so will the position of the underneath region under illumination wherefrom the back-scattered energy will be picked-up by the halfsphere entrance aperture 24a. This is clearly seen from the drawing in which the back-scattered light is indicated by numeral 28 when the excitation beam 22 falls at the angle α and by numeral 28g when the excitation beam 22g reaches the skin at an angle β. This technique permits the alternating exploration of different zones at different depths under the skin whereby different concentrations of glucose can be determined or monitored for a period of time. This is particularly useful for ascertaining the general shape of the background spectrum, i.e. the absorption of the medium in absence of glucose or when the concentration of glucose is insignificant or of low variability as is the case in the superficial layer of the epidermis. i.e. the stratum-corneum. Thus, the measurement of the absorption spectrum in the region 20a immediately under the skin surface will provide reference results which may be continuously or periodically compared to corresponding results obtained from deeper layers of the epidermis or the dermis, whereby useful data about the concentration of glucose in said deeper layers 20c can be obtained, this being directly proportional to the blood glucose concentration. The construction of the present embodiment also enables to block the light directly reflected by the skin surface at the impingement point. Indeed, such surface reflected component is parasitic since it comprises no glucose information and only contributes detrimentally to the background noise as in the embodiments of the prior art. Another advantage of the present invention's embodiment is that it obviates or minimizes possible disturbances caused by foreign substances contaminating the skin of the region under examination.

The electric signals provided from detectors 15 or 26 are analyzed and processed in circuits which constitute also part of the apparatus of the invention.

Figure 3:
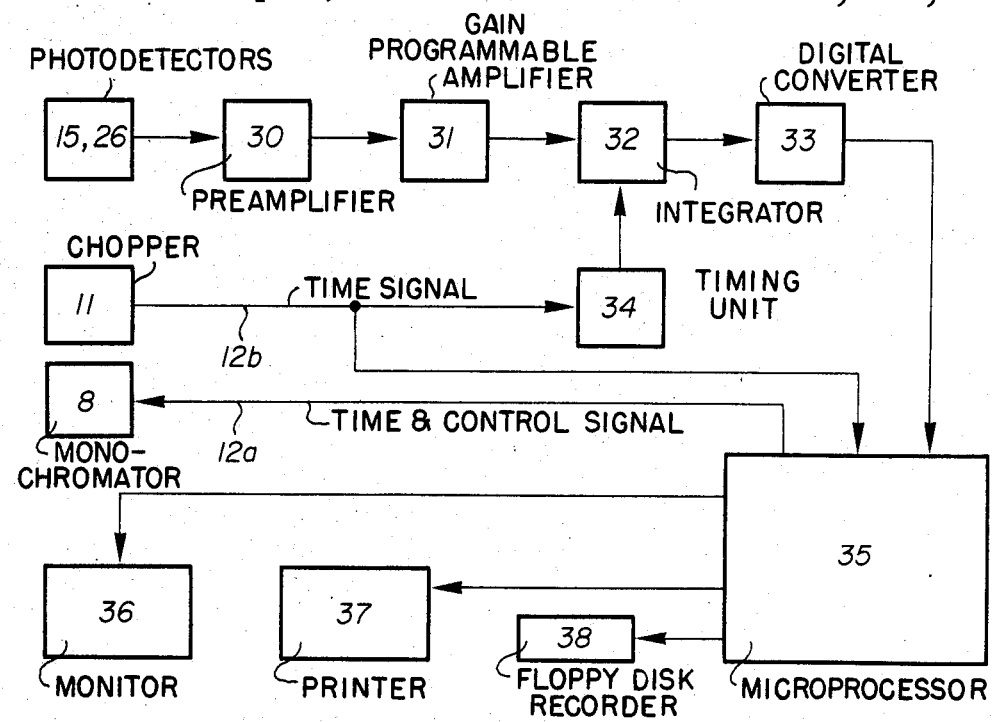
FIG. 3 represents schematically the components for processing the electrical signals obtained from the light gathered after being partly absorbed in the region of interest and for computing and converting said signals into useful readouts of glucose determination.

Such circuits shown on FIG. 3 comprise, starting from the photodetector 15 or 26 (depending on whether the embodiments of FIG. 1 or 2 are considered), a preamplifier 30 (for instance a JUDSON INFRARED Model 700 having an amplification of $10^7$ V/A) a gain programmable amplifier 31 (for instance with gain varying from 1 to 200), an integrator 32 for holding and averaging over noise and an analog to digital converter 33 (for instance a 16 bit unit). The integrator 32 is under control of a timing unit 34 timed by the clock of the chopper 11 (see FIG. 1).

The digital signal issuing from converter 33 comprising, in succession and according to a timing governed by said clock, the digitalized information relative to the background noise, the glucose measurement signal and the reference signals, is fed to a microprocessor 35 (for instance an APPLE II microcomputer) also controlled by said clock whereby the information is digested, computed according to a program of choice using one of the calculating methods disclosed heretofore and displayed or stored in terms of glucose determination data on either one or more of a monitor 36, a printer 37 or a floppy disk recorder 38. The microprocessor 35 also provides the signal for timing and controlling the wavelength scan or selection of the monochromator 8 (see line 12a).

REDUCTION TO PRACTICE

The following discloses a practical test effected according to transmissive technique (see FIG. 1). The data however apply equally well to the reflective technique illustrated by the device of FIG. 2. The measurements were carried out against an aqueous reference background such environment being sufficiently close to that overall body tissues to be fully significant. General physical considerations over absorption phenomena are also provided for reference.

The fundamental relation between optical absorbance and the concentration of the absorbing material is given by the Beer-Lambert law.

$$D = \log_{10}(I_o/I) = \epsilon \cdot C \cdot L$$

where
D = optical density, absorbance.
$I_o$ = intensity of incident light at wavelength λ.
I = intensity of light after passing through absorption cell.
C = concentration of the absorbing material (molar).
L = length of absorption path.
$\epsilon(\lambda)$ = extinction coefficient.

The validity of this relation is generally satisfactory if the radiation is monochromatic, if the concentrations of absorbing material are low, and if there are no significant molecular interactions, e.g. association, dissociation or structural changes for different concentrations. If the measurement phenomenon involves some significant degree of scattering, the above relation is no longer strictly valid and correction factors must be introduced to restore its usefulness. Reference to such modification can be found in GUSTAV KORTÜM'S book Reflexionsspektroskopie, SPRINGER Verlag (1969).

In the case of a mixture of m components, the Beer-Lambert law can be generalized and expanded to include absorbance of each of the components at each analytical wavelength.

$$D = \log_{10}(I_o/I) = L \cdot \sum_{i=1}^{m} \epsilon_i \cdot C_i$$

$\epsilon_i(\lambda)$ = specific absorbance of a component i which is wavelength dependent
$C_i$ = is the concentration defined as a mole fraction of the component i, so that $$\sum_{i=1}^{m} C_i = 1$$

$I_o$, $I$ and $L$ are defined as before.

In the experiments reported below, an apparatus such as that described with reference to FIGS. 1 and 3 was used, the ear portion being replaced by glucose solutions in water (pure water was used as reference). The parameters were: sample concentration of glucose=$C2$; concentration of water=$C1$ ($C1+C2=1$); path length for both pure water and solution=$L$; extinction coefficient of water=$\epsilon1$; extinction coefficient of glucose=$\epsilon2$.

The absorbances can be written in the two cases as:

$$D1 = L(\epsilon1 C1 + \epsilon2 C2) \text{ with } C1 + C2 = 1 \text{ (solution of glucose)}$$

$$D2 = L\epsilon1 \text{ (pure water)}$$

The absorbance difference $$(\Delta D = \log (I_{H_2O}) - \log (I_{glucose\text{-}solution}))$$

can then be written as $$\Delta D = D_2 - D_1$$

or $$\Delta D = LC_2(\epsilon_2 - \epsilon_1)$$

and $$C_2 = \frac{\Delta D}{L(\epsilon_2 - \epsilon_1)}$$

This equation shows that the concentration of glucose $C_2$ is proportional to the absorbance difference $\Delta D$ in the two samples since the constant factor $L(\epsilon_2-\epsilon_1)$ is known from operating conditions and kept constant.

As light of the incident intensity $I_o$ passes alternately through samples 1 and 2 causing intensities $I_1$ and $I_2$, this can be written:

$$C_2 \sim D = \log (I_o/I_1) - \log (I_o/I_2) = \log (I_2/I_1) = \log I_2 - \log I_1 \quad (1)$$

This means that it is sufficient to measure the difference of the absorbance in the samples 1 and 2. The incident intensity $I_o$ need not be measured.

Thus, the following three detected signals are processed in the microprocessor 35. (The proportionality constant between light intensity and detector signals is g).

$S_B = gB$: background when there is no light falling onto the samples. B is the background equivalent light intensity from ambient light plus the detector noise.

$S_1 = g(I_1+B)$: signal caused by test sample 1=(intensity $I_1$ plus background).

$S_2 = g(I_2+B)$: signal caused by reference sample 2=(intensity $I_2$ plus background).

For each sample, the difference between signal and background is taken, resulting in $\Delta S_1$ and $\Delta S_2$.

sample 1: $\Delta S_1 = g(I_1+B) - gB = gI_1$
sample 2: $\Delta S_2 = g(I_2+B) - gB = gI_2$ These operations were synchronized by the chopper system (500 Hz) to eliminate drifts of the background (zero) signal B which normally occur at very slow rate.

The quantities $\Delta S_1$ and $\Delta S_2$ were measured automatically for a number of times (100).

To find out the glucose concentration in sample 2, the absorbance value from water in sample 1 was used as a reference and the two values were subtracted from each other (see equation (1)):

$$\Delta D = \log I_2 - \log I_1 = \log (\Delta S_2/g) - \log (\Delta S_1/g)$$

$$\Delta D = \log \Delta S_2 - \log \Delta S_1 \quad (2)$$

The equation shows that the actual light intensities in equation 1 can be replaced by the electrical detector signals. The result is not dependent on the proportionality constant g.

The data processing program used in this embodiment is also able to compute the errors of a set of measurements by using classical algebraic equation of error propagation theory.

Four different glucose concentrations 0M, 0.05M, 0.5M and 1M and two different wavelengths 1100 nm (reference wavelength $\lambda R$) and 2098 nm (test wavelength $\lambda G$) were chosen.

At 1100 nm, the glucose spectrum is flat. The water absorbance has its lowest value. At about 2100 nm (more precisely 2098 nm), the glucose spectrum exhibits a characteristic absorption peak. The water absorbance here is about two absorbance units higher than an 1100 nm.

Figure 4:
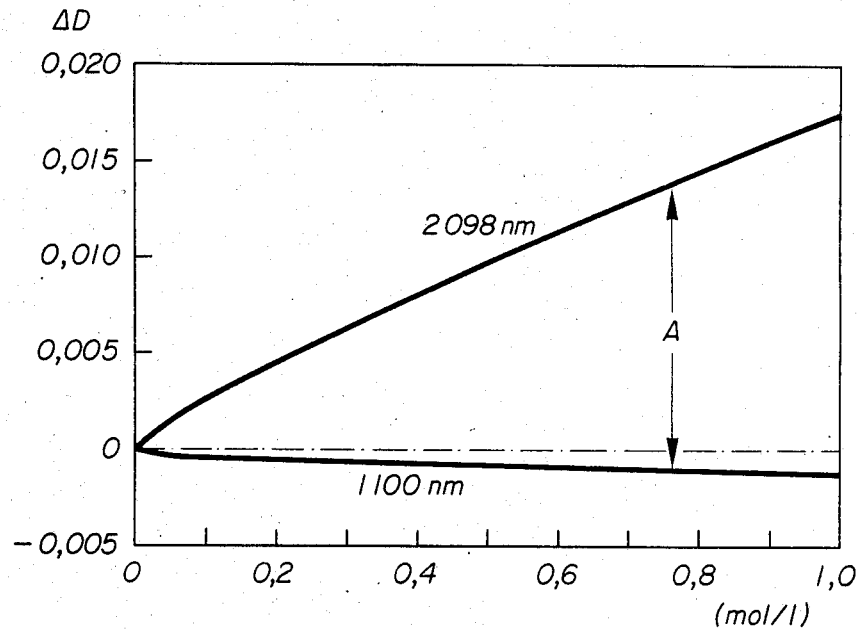
FIG. 4 represents a plot of absorption measurement data versus glucose concentration at both $\lambda G = 2100$ nm and $\lambda R = 1100$ nm.

In FIG. 4, the absorbance values $\Delta D$ are plotted for the two different wavelengths as a function of glucose concentration. The absorbance curve for 1100 nm falls slightly with concentration of glucose. As glucose has no specific absorption at this wavelength, essentially water is measured. With increasing glucose concentration, the water concentration is correspondingly reduced, so that the absorbance measured becomes smaller. At 2098 nm, a strong increase in absorbance with glucose concentration is observed. The curve is the result of two opposite acting effects: the reduced concentration of water causes an absorbance reduction which is similar to that for 1100 nm; the strong glucose absorbance at this wavelength causes an absorbance increase. As the glucose absorbance is about 13 times stronger, the result is an increase in absorbance. Thus, the net effect of glucose absorbance is approximately the vertical difference A between the curve for 2098 nm and the curve for 1100 nm. This confirms the soundness of the two wavelength methods embodiment, one at 2098 nm and the other at the reference independent wavelength of 1100 nm. Of course, similar methos using the other wavelengths disclosed in this specification are also possible and provide comparable results In addition to the aforementioned computations of measured results to estimate the concentrations of glucose, serum and water from absorbance measurements at various wavelengths, two other procedures for improved accuracy can be considered, i.e. regression and clustering. Details including differences and advantages of each technique are explained in the following reference and the references cited therein: J. B. Gayle, H. D. Bennett, "Consequences of Model Departures on the Resolution of Multicomponent Spectra by Multiple Regression and Linear Programming", Analytical Chemistry 50, 14, December 1978, p. 2085-2089. Clustering allows processing of more than one parameter (e.g., absorbance and skin depth). The starting clusters need not be data from pure solutions but can be mixtures. This is an advantage because serum normally always contains glucose so that reference data from serum without glucose are generally not easily obtainable.

Thus, in the case of a multi-component mixture, the main components of the body tissues competing with glucose as light absorbers in the spectral region of interest have characteristic absorptions distinct from the aforementioned selected typical glucose absorptions. Further, they also differ from glucose by their absolute concentration and by the time constant of their concentration variation. However, the general distribution of those "background" constituents is fairly constant. Therefore the ultimate glucose concentration can be obtained from absorbance measurements at various wavelengths.

We claim:

1. A spectrophotometric apparatus for determining the glucose concentration in body tissues transcutaneously and non-invasively, comprising:
    (a) a directional optical light source located external to the body, the spectral composition of the beam of light from said source being such that it can penetrate the skin to tissues below;
    (b) means for collecting light transmitted or diffusely reflected from said irradiated tissue;
    (c) means for detecting and converting into electrical signals light gathered from at least one band with a measuring signal wavelength $\lambda G$ of 1575, 1765, 2100 or 2270 + or − 15 nm, typical of the glucose absorption spectrum, and at least one band with a reference signal wavelength $\lambda R$ in the range of 1000 to 2700 nm, typical of the absorption spectrum of background tissue containing glucose but in which the absorption of glucose is nil or insignificant; and
    (d) means for transforming said electrical signals into data representing glucose determinations.

2. The apparatus of claim 1, further comprising a means for varying continuously or stepwise the incidence angle of said beam of light relative to the body surface, so that the depth under the skin surface wherefrom the light is gathered after absorption is varied.

3. The apparatus of claim 2, wherein said means for varying said incident angle comprises a mirror displacable in reflective relationship with said beam and positioned so that the reflected beam is always directed toward the same point on the skin.

4. The apparatus of claim 1, wherein said collecting means comprises the internal reflective surface of a halfsphere, said surface being coated with gold and/or a layer of barium sulfate containing paint.

5. A spectrophotometric method for the transcutaneous, non-invasive determination of glucose concentrations in body tissues, comprising the steps of:
    (a) irradiating a selected body portion with light from a directional optical lamp source;
    (b) collecting the resulting luminous energy (I) either transmitted or diffusively reflected by a sample volume of body tissue under the skin of said irradiated body portion, said collected light including at least one band with a measuring signal wavelength $\lambda G$ of 1575, 1765, 2100 or 2270 + or − 15 nm, typical of the glucose absorption spectrum, and at least one band with a reference signal wavelength $\lambda R$ in the range of 1000 to 2700 nm, typical of the absorption spectrum of background tissue containing glucose but in which the absorption of glucose is nil or insignificant;
    (c) converting band collected light into electrical signals IG and IR representing said measuring and reference bands, respectively; and
    (d) entering said electrical signals into an electronic computer for transformation into glucose concentrations.

6. The method according to claim 5, wherein a normalizing factor is established from the difference in absorption in said reference band when glucose is present and when glucose is absent or in insignificant quantities, absorbance values for the glucose as measured in said measuring band are normalized with said factor and said normalized values are used for said glucose determination.

7. The method according to claim 6, wherein said reference band corresponds to an isosbestic point selected in the range of 1100 to 1300 nm or in the regions straddling said $\lambda G$ bands.

8. The method according to claim 6, wherein the normalizing factor is established by alternately effecting absorption in said reference band first in a portion of body tissue where the amount of glucose is low or insignificant and, second, in a region of tissue in which the glucose concentration is to be analyzed.

9. The method according to claim 5, wherein said IG and IR signals are differentiated with respect to $\lambda$ within the area of said measuring and reference bands, respectively, the difference between the differentials being representative of said glucose determination.

* * * * *